United States Patent [19]

Tynan et al.

[11] 4,269,067

[45] May 26, 1981

[54] METHOD AND APPARATUS FOR FOCUSING ELASTIC WAVES CONVERTED FROM THERMAL ENERGY

[75] Inventors: Eugene E. Tynan, Mahopac; Russell W. Dreyfus, Mt. Kisco; Robert J. von Gutfeld, New York, all of N.Y.

[73] Assignee: International Business Machines Corporation, Armonk, N.Y.

[21] Appl. No.: 40,340

[22] Filed: May 18, 1979

[51] Int. Cl.³ .......................................... G01N 29/00
[52] U.S. Cl. .................................................... 73/643
[58] Field of Search ............... 73/601, 618, 620, 642, 73/643; 367/150, 151

[56] References Cited

U.S. PATENT DOCUMENTS

| | | | |
|---|---|---|---|
| 3,269,173 | 8/1966 | Von Ardenne | 73/642 |
| 3,322,231 | 5/1967 | Gournay | 367/141 |
| 3,532,181 | 10/1970 | Demaria et al. | 181/142 |
| 3,583,212 | 6/1971 | Nanney et al. | 73/579 |
| 3,903,990 | 9/1975 | Tannaka | 367/150 |
| 4,084,582 | 4/1978 | Nigam | 73/620 |
| 4,137,991 | 2/1979 | Melcher et al. | 73/643 |

OTHER PUBLICATIONS

R. M. White, "Generation of Elastic Waves by Transient Surface Heating", *Journal of Applied Physics*, vol. 34, No. 12, pp. 3559–3567, Dec. 1963.

*Primary Examiner*—Stephen A. Kreitman
*Attorney, Agent, or Firm*—Frank C. Leach, Jr.

[57] ABSTRACT

Pulsed light is applied through a plano concave lens to a thin metal film, which is evaporated on the concave side of the lens. The lens, which is formed of a high thermally insulating material such as glass, for example, and the film are disposed within a liquid such as water, for example. The pulsed light is absorbed by the metal film, which converts the thermal energy produced by the pulsed light into elastic waves in the form of acoustic waves and simultaneously focuses the acoustic waves on an object within the water at a selected focal plane. The metal film is as thin as possible, consistent with complete absorption of the light energy by the metal film, so as to utilize the high thermal expansion coefficient of the water.

28 Claims, 4 Drawing Figures

METHOD AND APPARATUS FOR FOCUSING ELASTIC WAVES CONVERTED FROM THERMAL ENERGY

The use of acoustic waves for non-destructive testing of articles and for medical diagnosis have previously been suggested. These acoustic waves have been produced primarily by piezoelectric transducers.

When a piezoelectric transducer has been employed to produce the acoustic waves, the piezoelectric transducer has had a plate shaped to focus the acoustic waves. One example of such an arrangement is shown in U.S. Pat. No. 4,084,582 to Nigam.

It also is well known to use a lens to focus acoustic waves. Examples of such an acoustic lens are found in U.S. Pat. No. 3,687,219 to Langlois, U.S. Pat. No. 3,903,990 to Tannaka, and an article by Atalar et al on pages 791–793 of the Dec. 15, 1977 (volume 31, No. 12) issue of Applied Physics Letters.

Another means for generating acoustic waves has been to employ a laser. The laser can be focused to such a small point of an acoustic wave generator that the acoustic waves are a very narrow beam. Thus, the use of a laser has enabled the acoustic waves to be produced from a source of thermal energy and directed to a selected area for non-destructive testing of an article or for medical diagnosis, for example, without requiring an acoustic lens for focusing the acoustic waves. Examples of such a laser are disclosed in U.S. Pat. No. 3,322,231 to Gournay, U.S. Pat. No. 3,532,181 to Demaria, and U.S. Pat. No. 3,583,212 to Nanney.

However, a laser is a relatively expensive device. Thus, its utilization as a source of thermal energy, even though no focusing of the acoustic waves is required due to the beam being focused prior to striking the acoustic wave generator, has been limited.

Pages 1277–1279 of IBM Technical Disclosure Bulletin, Volume 21, No. 3, disclose the use of a liquid having a high thermal expansion coefficient adjacent a metallic film, which converts pulsed thermal energy to elastic waves. This enables the major contribution to the elastic wave amplitude to be produced by the liquid because of its high thermal expansion coefficient.

The present invention is capable of using inexpensive sources of pulsed thermal energy such as a flash lamp, for example, to produce elastic waves through converting the thermal energy from the flash lamp to the elastic waves while simultaneously focusing the waves. Thus, the present invention enables a relatively low cost source of thermal energy to be employed for producing acoustic waves, which can be used for non-destructive testing, for example.

When utilized for non-destructive testing, for example, it is necessary for the acoustic waves to have a relatively large amplitude in order that the signals tested can be detected. The present invention meets this requirement through focusing the acoustic waves while efficiently converting the thermal energy to acoustic waves simultaneously.

The present invention accomplishes the simultaneous conversion and focusing by utilizing a curved thin film of metal. The curvature of the film of metal is selected to focus the acoustic waves so that the acoustic waves have the required energy density at the object to be tested in order to achieve effective non-destructive testing.

An object of this invention is to provide a unique transducer apparatus for converting thermal energy to focused elastic waves.

Another object of this invention is to test objects non-destructively.

A further object of this invention is to provide a method for converting thermal energy to focused elastic waves.

Still another object of this invention is to use focused elastic waves for non-destructive testing of objects.

The foregoing and other objects, features, and advantages of the invention will be apparent from the following more particular description of preferred embodiments of the invention, as illustrated in the accompanying drawings.

Figure 1:
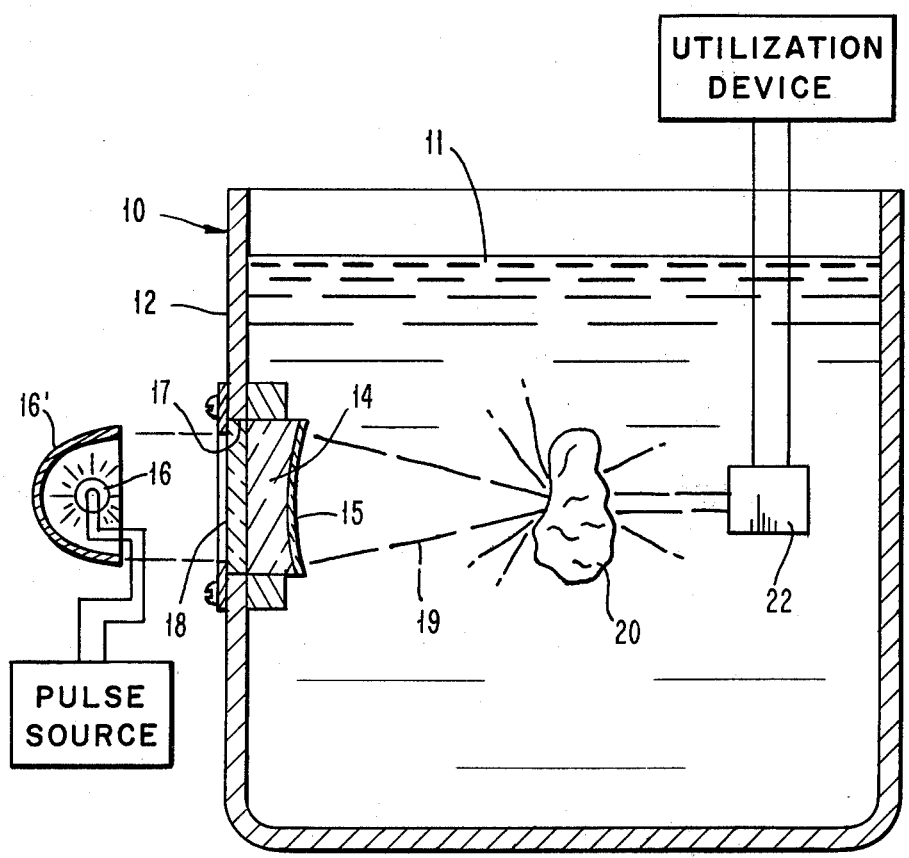
FIG. 1 is a schematic side sectional view of one embodiment of the apparatus of the present invention.

Referring to FIG. 1 of the drawings, there is shown a tank 10 having a liquid 11 such as water, for example, therein. It should be understood that other suitable liquids such as acetone, methanol, and ethanol, for example, may be employed if desired.

A wall 12 of the tank 10 has a plano concave lens 14, which is formed of a high thermal insulating material such as glass or quartz, for example, mounted on its inner surface. The concave side of the lens 14 has a film 15 of opaque metal bonded thereto by suitable means such as evaporating the film 15 of metal thereon.

The metal of the film 15 can be any suitable material for converting thermal energy in the form of light into elastic energy in the form of acoustic waves. The metal of the film 15 is preferably a refractory metal such as molybdenum, tungsten, platinum, or vanadium, for example.

Thus, the film 15 of metal is clamped between the lens 14, which is a body of solid material, and the liquid 11. This increases the conversion efficiency of the film 15 of metal.

Light from a relatively weak light source such as a flash lamp 16, for example, is directed by a reflector 16' through an opening 17, which has a transparent material 18 therein, in the wall 12 to the lens 14 for conversion into elastic energy (acoustic waves) and focusing of the acoustic waves by the curved film 15 of metal. The thickness of the film 15 of metal is selected so that it absorbs as much of the light energy as possible while being as thin as possible to cause most of the heat from the light to be applied to the liquid 11 which more efficiently converts the thermal energy into elastic energy due to its higher thermal expansion coefficient.

The thickness of the metal film 15 should be at least the reciprocal of the optical absorption constant of the metal of the film 15. Thus, the thickness of the metal of the film 15 is within the range of 300 Angstroms to 500 Angstroms.

The curvature of the film 15 of metal is the same as the curvature of the concave side of the lens 14 to which the film 15 is bonded. This curvature is selected so that acoustic waves 19, which are generated in the liquid 11 as a result of the thermal energy produced by the light from the flash lamp 16 striking the metal film 15, are focused to strike an object 20 which is to be non-destructively tested. It should be understood that the object 20 is supported within the liquid 11 in the tank 10 by any suitable means (not shown). While the object 20 is disclosed as being within the liquid 11, it should be understood that it could be exterior of the liquid 11, but this would result in the focus of the acoustic waves 19 on the object 20 not being as sharp. This also requires there to be some acoustic coupling between the tank 10 and the ambient surrounding the object 20.

The curvature of the metal film 15 focuses the acoustic wave 19 to converge the energy on the object 20. Thus, this produces a higher density of energy at the object 20.

A transducer 22 is disposed within the liquid 11 to detect the acoustic waves 19 after having struck the object 20. One suitable example of the transducer 22 is a B scan transducer sold by KB-Aerotech Division of Krautkramer-Branson Inc., Lewistown, Pa. as part of the Aerotech BST series. Any other suitable detecting transducer may be employed.

The waves detected by the transducer 22 are compared with reference signals, which have previously been determined. This comparison determines whether the object 20 is satisfactory or not.

The reference signals are developed through use of a relatively flawless piece of the material to be tested, for example. The relatively flawless piece is disposed within the liquid 11 at the location of the object 20, and the reference signals are produced therefrom by obtaining a set of curves, for example, through analyzing the frequencies of the signals received at the transducer 22.

While the transducer 22 has been shown as having the acoustic waves 19 pass through the object 20 and then be detected by the transducer 22, it should be understood that such is not necessary. That is, the transducer 22 could receive reflected waves from another of the objects 20 rather than having the waves pass through the object 20. This would require the transducer 22 to be disposed forward of the object 20 but to its side so as to not be in the path of the waves 19 focused from the curved film 15 of metal.

While the present invention has shown and described the source of thermal energy as being the pulsed flash lamp 16, it should be understood that any source of pulsed thermal energy could be utilized. Thus, a laser, a pulsed carbon arc, an electron beam, an X-ray, or an atomic beam, for example, could be employed as the source of pulsed thermal energy. However, all of these are more expensive than the flash lamp 16, and the present invention enables a weak and relatively inexpensive source of pulsed thermal energy to be utilized.

While the apparatus of the present invention has shown and described the film 15 of metal as being disposed within the liquid 11, it should be understood that it could be disposed within any fluid.

However, gases such as air, for example, do not have a high thermal expansion coefficient as do liquids such as water, acetone, ethanol, or methanol, for example. Thus, the amplitude of the acoustic waves 19 would be much smaller and more difficult to detect.

In addition to having the film 15 of metal disposed in a fluid, it should be understood that the film 15 of metal also could be mounted within a body of solid material. The body would have to be cut in some manner as the focal plane of the acoustic waves 19 at which the object 20 is to be located so that the object 20 could be inserted within the body.

While the apparatus of the present invention has shown the flash lamp 16 as being directed to the curved film 15 of metal through the lens 14, it should be understood that various types of lens arrangements could be employed between the flash lamp 16 and the lens 14 to maximize the application of the light energy from the flash lamp 16 to the lens 14. This light maximizing arrangement would be disposed exterior of the tank 10.

While the flash lamp 16 has been shown and described as being exterior of the tank 10, it should be understood that the flash lamp 16 could be within the liquid 11. This would be particularly true where the medium is not the liquid 11 but is a gas or a solid.

It should be understood that the radius of curvature of the concave side of the lens 14 is selected to provide the focusing at the desired distance from the film 15 of metal. This is determined by the elastic velocity of the material of the lens 14 and the liquid 11.

For most efficient conversion of the thermal energy to elastic waves, the film 15 of metal needs to be clamped between the lens 14 and the liquid 11 at their interface as shown in U.S. Pat. No. 4,137,991 to Melcher et al, for example. However, it should be understood that the present invention will produce elastic waves in the liquid 11 even if the film 15 of metal is not clamped but the amplitude of the waves will be much smaller and hence the wave more difficult to detect.

Figure 2:
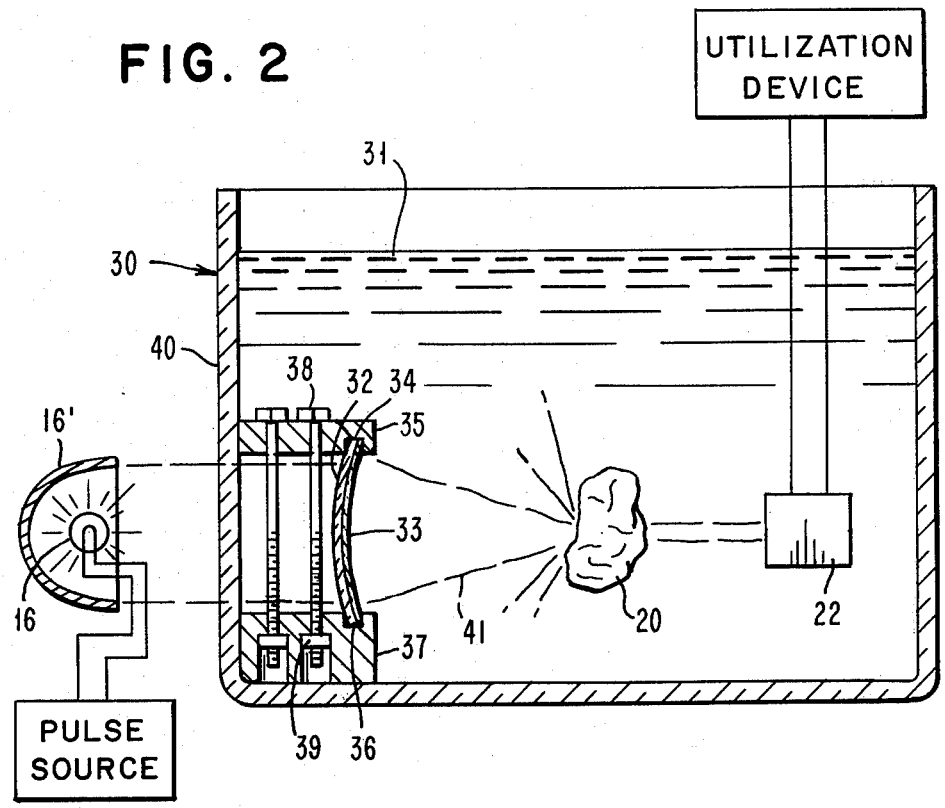
FIG. 2 is a schematic side sectional view of a modification of the apparatus of the present invention.

Referring to FIG. 2 of the drawings, there is shown a tank 30 having a liquid 31 such as water, for example, therein. It should be understood that other suitable liquids such as acetone, methanol, and ethanol, for example, may be employed if desired.

The tank 30 is preferably formed of glass. However, the tank 30 may be formed of any other suitable transparent material.

The tank 30 has a lens 32, which is an arcuate portion of a cylinder, disposed therein. The lens 32 is formed of a strip of Mylar, which is a high thermal insulating material, having a thickness of five to ten mils.

The lens 32 has a film 33 of opaque metal bonded thereto by suitable means such as evaporating the film 33 of metal thereon. The metal of the film 33 may be of any of the same metals as the metal of the film 15.

The lens 32 has one edge supported within a groove 34 in a clamp 35 and its other end supported in a groove 36 in a clamp 37. Clamping screws 38 extend through the clamps 35 and 37 with each of the screws 38 having a nut 39 cooperating therewith. Accordingly, by tightening the clamping screws 38, the clamp 35 is moved closer to the clamp 37 to increase the curvature of the lens 32 and change the effective focal length.

In the same manner as discussed with respect to FIG. 1, the flash lamp 16 has light reflected therefrom by the reflector 16' and through a wall 40 of the tank 30 to the lens 32. The thickness of the film 33 of metal is selected in the same manner as the thickness of the metal of the film 15 is selected. The lens 32 and the film 33 of metal have a radius of curvature selected through controlling the distance between the clamps 35 and 37 so that acoustic waves 41, which are generated in the liquid 31 as a result of thermal energy produced by the light from the flash lamp 16 striking the metal film 33, are focused to strike the object 20 which is to be non-destructively tested. The waves 41 are focused to a line, which is the axis of the cylinder of which the lens 32 is an arcuate portion.

The remainder of the operation of the apparatus of FIG. 2 is the same as that discussed with respect to FIG. 1. Thus, the apparatus of FIG. 2 utilizes a relatively inexpensive lens in comparison to that of the apparatus of FIG. 1. The use of the movable clamp 35 through the clamping screws 38 enables easy change of the effective focal length of the lens 32.

Figure 3:
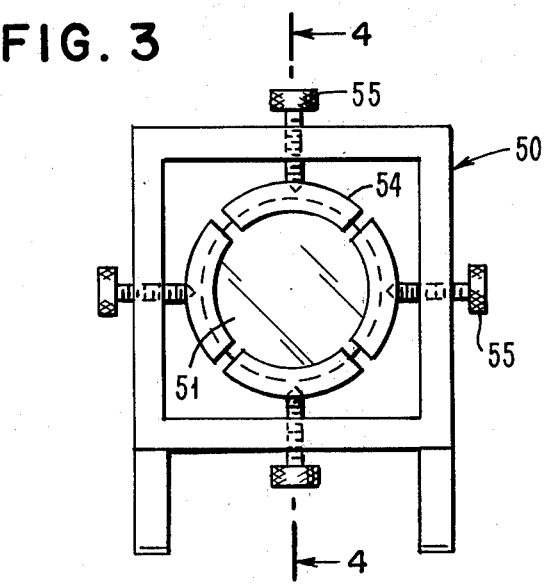
FIG. 3 is a schematic elevational view of a further form of the apparatus of the present invention.
Figure 4:
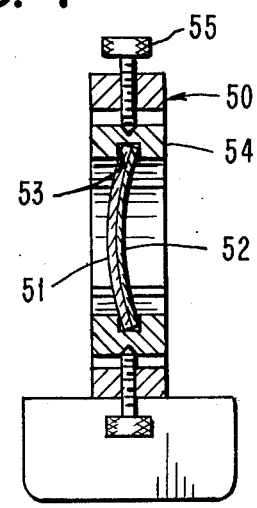
FIG. 4 is a sectional view of the apparatus of FIG. 3 and taken along line 4—4 of FIG. 3.

Referring to FIGS. 3 and 4, there is shown a frame 50 for disposition within the tank 30 of FIG. 2. The frame 50 has a lens 51, which is formed of the same material as the lens 32. The lens 51 has a film 52 of metal bonded thereto in the same manner as the film 33 of metal is bonded to the lens 32. The circumferential edge of the lens 51 is disposed within an arcuate groove 53 in each of a plurality of arcuate edge clamps 54.

A screw 55 exerts pressure on each of the edge clamps 54. Thus, the lens 51 has its radius of curvature easily increased or decreased to change the effective focal length. The lens 51 functions in the same manner as the lens 14 or the lens 32.

The apparatus of FIGS. 3 and 4 has the same low cost fabrication advantage as does the lens 32 of FIG. 2. Additionally, it also has the advantage of having the effective focal length easily changed through changing the pressure on the circumference of the edge clamps 54.

It should be understood that the apparatus of FIG. 2 or the apparatus of FIGS. 3 and 4 could be disposed within the tank 10. Of course, this would require the disposition of the lens 32 or the lens 51 in alignment with the opening 17 in the same manner as the lens 14. Likewise, the apparatus of FIG. 1 could be utilized with the transparent tank 30 of FIG. 2 if desired.

An advantage of this invention is that a relatively inexpensive source of thermal energy may be employed for producing detectable elastic waves. Another advantage of this invention is that an object may be tested without being damaged. A further advantage of this invention is that elastic waves of relatively large amplitude are generated.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A transducer apparatus including:
   a medium;
   and unitary converting means within said medium to simultaneously convert pulses of thermal energy into acoustic waves for transmission through said medium and focus the acoustic waves.

2. The apparatus according to claim 1 in which said medium is a liquid.

3. The apparatus according to claim 2 in which said unitary converting means includes:
   a body of a solid material having a curved surface;
   and a thin film of metal bonded to said curved surface of said body to have substantially the same radius of curvature, said film having its surface remote from said body in contact with said liquid.

4. The apparatus according to claim 3 in which the pulses of thermal energy are pulses of light.

5. The apparatus according to claim 1 in which said unitary converting means includes:
   a body of a solid material having a curved surface;
   and a thin film of metal bonded to said curved surface of said body to have substantially the same radius of curvature, said film having its surface remote from said body in contact with said medium.

6. The apparatus according to claim 5 in which the pulses of thermal energy are pulses of light.

7. The apparatus according to claim 1 including means to detect acoustic waves produced by the acoustic waves striking an object to be tested.

8. The apparatus according to claim 7 in which said medium is a liquid.

9. The apparatus according to claim 8 in which said unitary converting means includes:
   a body of a solid material having a curved surface;
   and a thin film of metal bonded to said curved surface of said body to have substantially the same radius of curvature, said film having its surface remote from said body in contact with said liquid.

10. The apparatus according to claim 9 in which the pulses of thermal energy are pulses of light.

11. The apparatus according to claim 7 in which said unitary converting means includes:
    a body of a solid material having a curved surface;
    and a thin film of metal bonded to said curved surface of said body to have substantially the same radius of curvature, said film having its surface remote from said body in contact with said medium.

12. The apparatus according to claim 11 in which the pulses of thermal energy are pulses of light.

13. A method for converting thermal energy to focused acoustic waves within a medium including:
    directing pulses of thermal energy to a selected area within the medium;
    and converting the pulses of thermal energy into acoustic waves at the selected area while simultaneously focusing the acoustic waves.

14. The method according to claim 13 in which the medium is a liquid.

15. The method according to claim 14 in which the pulses of thermal energy are pulses of light.

16. The method according to claim 15 including:
    disposing an object to be tested at a selected focal area of the focused acoustic waves;
    and sensing the effect on the acoustic waves by the object so that the object is non-destructively tested.

17. The method according to claim 14 including:
    disposing an object to be tested at a selected focal area of the focused acoustic waves;
    and sensing the effect on the acoustic waves by the object so that the object is non-destructively tested.

18. The method according to claim 13 including:
    disposing an object to be tested at a selected focal area of the focused acoustic waves;
    and sensing the effect on the acoustic waves by the object so that the object is non-destructively tested.

19. A transducer apparatus including:
    a medium;
    unitary converting means within said medium to simultaneously convert pulses of thermal energy into acoustic waves for transmission through said medium and focus the acoustic waves;
    said unitary converting means including:
    a body of a solid material having a curved surface;
    and a thin film of metal bonded to said curved surface of said body to have substantially the same radius of curvature, said film having its surface remote from said body in contact with said medium;

and changing means to selectively change the radius of curvature of each of said film and said curved surface of said body to change the focusing of the acoustic waves.

20. The apparatus according to claim 19 in which said changing means includes:

a plurality of engaging means to engage spaced portions of the periphery of each of said film and said body;

and moving means to move said engaging means relative to each other to change the radius of curvature of each of said film and said body.

21. The apparatus according to claim 20 in which said engaging means of said changing means includes at least two clamping means, each of said clamping means having a groove to receive a portion of the periphery of each of said film and said body.

22. The apparatus according to claim 21 in which:

said clamping means includes two oppositely disposed clamping means;

and said moving means includes means connected to each of said clamping means to simultaneously move said clamping means towards or away from each other to change the radius of curvature of each of said film and said body.

23. The apparatus according to claim 22 in which the medium is a liquid.

24. The apparatus according to claim 21 in which:

each of said film and said body has a circular periphery;

said clamping means includes at least three clamping means engaging portions of the periphery of each of said film and said body;

and said moving means includes means cooperating separately with each of said clamping means to move each of said clamping means towards or away from the center of said film and said body to change the radius of curvature of each of said film and said body.

25. The apparatus according to claim 24 in which the medium is a liquid.

26. The apparatus according to claim 21 in which the medium is a liquid.

27. The apparatus according to claim 20 in which the medium is a liquid.

28. The apparatus according to claim 19 in which the medium is a liquid.

* * * * *